(12) United States Patent
Daniel et al.

(10) Patent No.: US 12,205,448 B2
(45) Date of Patent: *Jan. 21, 2025

(54) SYSTEMS, METHODS AND DEVICES FOR THE RAPID ASSESSMENT AND DEPLOYMENT OF APPROPRIATE MODULAR AID SOLUTIONS IN RESPONSE TO DISASTERS

(71) Applicants: Simon R. Daniel, Farnham (GB); Timothy W. Coleman, Palm Beach, FL (US); Yitzhack Schwartz, Haifa (IL); Zubin Rustom Wadia, White Plains, NY (US); Justyna Zander, Berlin (DE)

(72) Inventors: Simon R. Daniel, Farnham (GB); Timothy W. Coleman, Palm Beach, FL (US); Yitzhack Schwartz, Haifa (IL); Zubin Rustom Wadia, White Plains, NY (US); Justyna Zander, Berlin (DE)

(73) Assignees: Simon R. Daniel, Farnham (GB); Timothy W. Coleman, FL (US); Yitzhack Schwartz, Haifa (IL); Zubin Rustom Wadia, NY (US); Justyna Zander, Berlin (DE)

(*) Notice: Subject to any disclaimer, the term of this patent is extended or adjusted under 35 U.S.C. 154(b) by 0 days.

This patent is subject to a terminal disclaimer.

(21) Appl. No.: 17/988,619

(22) Filed: Nov. 16, 2022

(65) Prior Publication Data
US 2023/0081755 A1 Mar. 16, 2023

Related U.S. Application Data

(63) Continuation of application No. 17/060,619, filed on Oct. 1, 2020, now Pat. No. 11,508,228, which is a
(Continued)

(30) Foreign Application Priority Data

Aug. 27, 2009 (GB) ...................... 0914962

(51) Int. Cl.
*G08B 21/02* (2006.01)
*G08B 25/01* (2006.01)
(Continued)

(52) U.S. Cl.
CPC ........... *G08B 21/02* (2013.01); *G08B 25/016* (2013.01); *H04L 12/1895* (2013.01);
(Continued)

(58) Field of Classification Search
CPC ....... G08B 21/02; G08B 25/016; H04L 51/58; H04L 12/1895; H04L 12/189; B64C 39/024; H04Q 9/00; B64U 2101/60
(Continued)

(56) References Cited

U.S. PATENT DOCUMENTS 3,724,788 A * 4/1973 Petry ........................ B64D 1/02
244/137.3
4,570,733 A * 2/1986 Star ........................... B60P 3/14
180/41
(Continued)

*Primary Examiner* — Zhen Y Wu
(74) *Attorney, Agent, or Firm* — Conley Rose, P.C.

(57) ABSTRACT

A disaster response system includes a communication infrastructure including a plurality of sensor assemblies configured to generate data indicative of at least one of environmental conditions, motion, position, chemical detection, and medical information; and wirelessly provide the generated data to the communication infrastructure. The system also includes an incident command infrastructure configured to exchange data with the communication infrastructure; and detect an incident based on the data from the sensor assemblies. The system also includes an unmanned aerial vehicle (UAV) configured to deliver a payload in response to the detected incident.

18 Claims, 6 Drawing Sheets

Related U.S. Application Data continuation of application No. 15/951,279, filed on Apr. 12, 2018, now abandoned, which is a continuation of application No. 14/633,530, filed on Feb. 27, 2015, now abandoned, which is a continuation of application No. 12/870,117, filed on Aug. 27, 2010, now abandoned.

(51) Int. Cl.
*H04L 12/18* (2006.01)
*H04L 51/58* (2022.01)
*H04Q 9/00* (2006.01)
*B64U 101/69* (2023.01)

(52) U.S. Cl.
CPC ............... *H04L 51/58* (2022.05); *H04Q 9/00* (2013.01); *B64U 2101/69* (2023.01); *B64U 2201/20* (2023.01); *H04L 12/189* (2013.01)

(58) Field of Classification Search
USPC .......................................... 340/870.07, 870
See application file for complete search history.

(56) References Cited

U.S. PATENT DOCUMENTS

| | | | | | |
|---|---|---|---|---|---|
| 5,340,056 | A * | 8/1994 | Guelman | ............... | F41G 7/2253 244/3.16 |
| 5,521,817 | A * | 5/1996 | Burdoin | ............... | G05D 1/0027 701/3 |
| 5,847,679 | A * | 12/1998 | Yee | ............... | G01S 19/17 701/484 |
| 5,878,979 | A * | 3/1999 | Fisher | ............... | B64D 17/80 244/49 |
| 6,056,237 | A * | 5/2000 | Woodland | ............... | B64D 1/02 244/49 |
| 6,084,510 | A * | 7/2000 | Lemelson | ............... | G08G 1/164 382/104 |
| 6,259,399 | B1 * | 7/2001 | Krasner | ............... | H01Q 21/28 342/357.57 |
| 6,269,763 | B1 * | 8/2001 | Woodland | ............... | B63B 35/66 43/4.5 |
| 6,655,636 | B1 * | 12/2003 | Moritz | ............... | B64D 1/08 244/137.1 |
| 7,123,169 | B2 * | 10/2006 | Farmer | ............... | H04B 7/18506 455/431 |
| 8,040,246 | B2 * | 10/2011 | Graves | ............... | A61B 5/681 340/573.1 |
| 8,094,834 | B1 * | 1/2012 | Brungart | ............... | H04S 7/304 381/26 |
| 8,125,371 | B1 * | 2/2012 | Daniel | ............... | F41A 17/08 342/52 |
| 8,917,176 | B2 * | 12/2014 | Raj | ............... | G08B 21/02 340/506 |
| 9,307,383 | B1 * | 4/2016 | Patrick | ............... | B64U 30/299 |
| 2002/0060267 | A1 * | 5/2002 | Yavnai | ............... | B64U 60/40 180/7.4 |
| 2003/0209631 | A1 * | 11/2003 | Harding | ............... | G05D 1/12 244/3.1 |
| 2003/0212478 | A1 * | 11/2003 | Rios | ............... | G05D 1/0094 701/13 |
| 2003/0213358 | A1 * | 11/2003 | Harding | ............... | G05D 1/12 89/1.11 |
| 2004/0008125 | A1 * | 1/2004 | Aratow | ............... | G08B 31/00 340/870.07 |
| 2004/0023635 | A1 * | 2/2004 | Impson | ............... | H04L 12/66 455/404.1 |
| 2004/0266390 | A1 * | 12/2004 | Faucher | ............... | H04W 4/90 455/456.2 |
| 2005/0051667 | A1 * | 3/2005 | Arlton | ............... | G08B 13/19621 244/17.11 |
| 2005/0077424 | A1 * | 4/2005 | Schneider | ............... | G01S 11/08 701/532 |
| 2005/0086004 | A1 * | 4/2005 | Smith | ............... | G08B 27/006 702/3 |
| 2005/0127242 | A1 * | 6/2005 | Rivers, Jr. | ............... | B64D 1/02 244/137.1 |
| 2005/0197749 | A1 * | 9/2005 | Nichols | ............... | G05D 1/0202 701/3 |
| 2005/0231425 | A1 * | 10/2005 | Coleman | ............... | G08G 1/20 342/385 |
| 2006/0015254 | A1 * | 1/2006 | Smith | ............... | H04W 4/02 340/905 |
| 2006/0081665 | A1 * | 4/2006 | Nguyen | ............... | A63H 27/10 224/267 |
| 2006/0085106 | A1 * | 4/2006 | Gaudiano | ............... | G01C 11/00 701/26 |
| 2006/0114324 | A1 * | 6/2006 | Farmer | ............... | G01S 7/003 709/201 |
| 2006/0146053 | A1 * | 7/2006 | Gatewood, Jr. | ............... | G06T 17/05 345/440 |
| 2006/0186622 | A1 * | 8/2006 | Darling, III | ............... | B62B 13/18 280/35 |
| 2006/0237494 | A1 * | 10/2006 | Fichera | ............... | A45F 5/021 224/669 |
| 2007/0029439 | A1 * | 2/2007 | Merems | ............... | B64D 1/02 244/7 R |
| 2007/0112705 | A1 * | 5/2007 | Mardirossian | ............... | H04B 7/18504 706/24 |
| 2007/0131822 | A1 * | 6/2007 | Stallard | ............... | G05D 1/104 244/190 |
| 2007/0159321 | A1 * | 7/2007 | Ogata | ............... | A61B 5/0002 340/539.12 |
| 2007/0252035 | A1 * | 11/2007 | Hubbard, Jr. | ............... | G05D 1/105 244/75.1 |
| 2008/0052621 | A1 * | 2/2008 | Oliverio | ............... | G06Q 10/10 715/700 |
| 2008/0074238 | A1 * | 3/2008 | Kodialam | ............... | H04L 43/0882 340/10.2 |
| 2008/0139165 | A1 * | 6/2008 | Gage | ............... | H04W 76/50 455/414.1 |
| 2008/0261653 | A1 * | 10/2008 | Hara | ............... | H04M 1/72445 455/344 |
| 2008/0294019 | A1 * | 11/2008 | Tran | ............... | G16H 15/00 600/301 |
| 2009/0143045 | A1 * | 6/2009 | Graves | ............... | A61B 5/1113 455/404.1 |
| 2009/0170467 | A1 * | 7/2009 | Nowlan | ............... | H04W 4/90 455/404.1 |
| 2009/0170529 | A1 * | 7/2009 | Kane | ............... | H04W 4/90 455/456.3 |
| 2009/0195401 | A1 * | 8/2009 | Maroney | ............... | G06V 20/52 340/686.6 |
| 2009/0196234 | A1 * | 8/2009 | Greene | ............... | H04L 69/08 370/328 |
| 2009/0205845 | A1 * | 8/2009 | Hoffman | ............... | A62C 3/025 701/2 |
| 2010/0109865 | A1 * | 5/2010 | Armstrong | ............... | G01S 19/51 340/539.13 |
| 2010/0141385 | A1 * | 6/2010 | Shiau | ............... | H04B 5/77 340/10.1 |
| 2010/0156171 | A1 * | 6/2010 | Sechrist | ............... | B60R 16/03 307/9.1 |
| 2010/0198514 | A1 * | 8/2010 | Miralles | ............... | F41G 7/2293 701/302 |
| 2010/0217096 | A1 * | 8/2010 | Nanikashvili | ............... | A61B 5/6822 600/301 |
| 2010/0273504 | A1 * | 10/2010 | Bull | ............... | H04K 3/65 455/456.1 |
| 2011/0017863 | A1 * | 1/2011 | Goossen | ............... | F41G 7/303 244/3.14 |
| 2011/0068926 | A1 * | 3/2011 | Jong | ............... | A61B 5/0002 340/573.1 |
| 2012/0256762 | A1 * | 10/2012 | Greenberger | ............... | H04Q 9/00 340/870.03 |

* cited by examiner

SYSTEMS, METHODS AND DEVICES FOR THE RAPID ASSESSMENT AND DEPLOYMENT OF APPROPRIATE MODULAR AID SOLUTIONS IN RESPONSE TO DISASTERS

CROSS-REFERENCE TO RELATED APPLICATIONS

This application is a continuation of U.S. patent application Ser. No. 17/060,619 filed Oct. 1, 2020, which is a continuation of U.S. patent application Ser. No. 15/951,279, filed Apr. 12, 2018, which is a continuation of U.S. patent application Ser. No. 14/633,530, filed Feb. 27, 2015, which is a continuation of U.S. patent application Ser. No. 12/870,117, filed Aug. 27, 2010, which claims the benefit of priority to Great Britain Patent Application No. GB0914962.6, filed Aug. 27, 2009, the content of each being hereby incorporated by reference in their entirety for all purposes.

FIELD OF THE DISCLOSURE

This disclosure relates generally to systems, devices and methods for global disaster response, more particularly to the rapid detection, qualified assessment and monitoring of disasters and electronic triage of victims, communication, alert and evacuation systems, provision of suitable modular sensing or aid solutions, and their rapid deployment via delivery platforms such as mobile applications and networks, remote operated vehicles (unmanned aerial sea or land systems) or targeted air delivery, automated or robotic support means, or pre-deployment.

BACKGROUND

Natural disasters, such as earthquakes, tsunamis and hurricanes and other mass emergencies represent significant threats to mankind in terms of mortality, injuries, chaotic reaction of civilians and response organizations. With over half the world population now living in urban areas, the complexity of the response phase is also increasing in terms of search and rescue across a damaged three-dimensional cityscape, rapidly and effectively assisting large numbers of casualties or citizens across a wide area with medical aid or evacuation advice, loss of main communications networks, delay or damage to response infrastructure-transport, energy and medical facilities, and difficulties in logistics and distribution of aid resources. Similarly, with large scale disasters the mass displacement, refugee volumes and need for substantial sustenance in terms of large scale medical assistance, food, clean water, habitat and infrastructure in the days following a disaster is significant and can result in considerable threat to life, medical needs and other problems if not addressed and managed properly.

For example, in a major earthquake, damage can be sustained over thousands of square kilometers, resulting in millions of people impacted or displaced, loss of transport/access and communications infrastructure, electricity and medical facilities within the region, and consequential fires, flooding, aftershock damage, sanitation/water issues, habitat and food crises. In the 2008 Sichuan 7.9 Earthquake some 70,000 people were killed, and another 5 m made homeless. FEMA estimate that an afternoon 8.3 magnitude earthquake on the San Andreas fault could kill 11,000 people instantly and over 44,000 needing hospitalization. Similarly, in the Katrina Hurricane in New Orleans, groups of people did not evacuate and were left isolated creating clusters in need but no emergency personnel were able to reach them for several days. War zones and famines also create huge displacements and volumes of refugees, and significant medical and sustenance challenges in aid camps.

Various proposals have been made to improve emergency broadcast systems, or methods of directing people to safety during an emergency whereby a wireless device extracts directional information from an emergency signal or receives notifications and evacuation plan, e.g., U.S. application Ser. No. 11/965,204 by Kane et al., U.S. application Ser. No. 11/966,536 by Nowlan et al., U.S. application Ser. No. 12/069,899 by Mendelson, U.S. application Ser. No. 12/281,456 by Huber, and U.S. application Ser. No. 12/315,848 by Norp et al.; Distributing warning messages to plurality of mobile devices within a defined geographic location was also disclosed in U.S. application Ser. No. 11/862,742 by Langsenkamp et al.

However, none of these solutions addresses the challenging scenario of failing networks during or after a disaster, which the described embodiments address by using pre-caching of information and novel burst-SMS condensed message structures sent to selected subpopulations according to their geo-location to provide advice, resources and guided evacuation, and enable incident command to better direct evacuation with limited network bandwidth.

Systems for professional incident response teams have also been proposed, e.g., U.S. application Ser. No. 12/410,003 by Lewis, for automatically uploading wirelessly maps and preprogrammed instructions to a mobile phone prior to entering a disaster zone to support teams focused on both short and long term recovery operations and relies on stored data and base unit availability, but does not address real-time information or data for civilian usage, or the benefits of the described embodiments in enabling any user of mobile phone who is already present in a disaster zone to access relevant data stored on the phone itself. The phone would be continuously synching local maps, local floor-plans, and points of interests (medical resource, toxic and other hazards) into its local memory cache upon entry into new zones, risk areas or buildings. Said local data essentially being 'rehydrated' or refreshed seamlessly in the background, and expandable or unlocked and made available to the user upon a disaster even if the network is down.

Currently there are systems for remote monitoring of personnel, especially for monitoring the well-being of military personnel on the battlefield and during training exercises. See e.g., U.S. Pat. No. 6,198,394 by Jacobsen et al.; Similarly, sensor-based patient monitoring and tracking is already used extensively in hospitals. During an emergency event involving mass casualty rapid e-triage (electronic counting and sorting) of patients by early responders, rather than usage of paper tags, is an essential early step in the emergency response process. Such solutions were proposed in U.S. application Ser. No. 11/741,756 by Gao et al., U.S. application Ser. No. 11/895,762 by Vasquez et al., and U.S. application Ser. Nos. 12/213,672, 12/213,673 and 12/213,675 by Graves et al.

Early feasibility studies of e-triage as performed by professional first responders were indeed very promising. See Killeen J P. A wireless first responder handheld device for rapid triage, patient assessment and documentation during mass casualty incidents. AMIA Annu Symp Proc 2006: 429-33; Massey T et al. The Design of a Decentralized Electronic Triage System. AMIA Annu Symp Proc 2006: 544-548; Gao T, White D. A Next generation electronic triage to aid mass casualty emergency medical response. Conf Proc IEEE Eng Med Biol Soc 2006; Suppl: 6501-4;

and Jokela et al. Implementing RFID technology in a novel triage system during a simulated mass casualty situation. Int J Electron Healthc 2008; 4 (1): 105-18. Each of these references are hereby incorporated by reference in their entirety for all purposes.

Such e-triage would be extremely valuable in terms of rapidly generating trusted data in terms of situational awareness, allocation of necessary resources and prioritization for evacuation. Attaching a wristband containing machine readable information to each victim of the group was proposed as a method for rapid tracking of trauma victims and ascertaining continuity of treatment. See e.g., U.S. application Ser. No. 12/132,668 by Carlton. In various embodiments, the provision of electronic bracelets would further enable real-time monitoring of all casualties, optimal continuous treatment at all levels and generation of reliable statistics for governmental disaster database. It is foreseeable that novel electronic triage performed by first-on-scene professional volunteers or by eligible civilian volunteers like Community Emergency Response Teams would further facilitate an even faster situational awareness and improve the immediate care. The data generated by the volunteers would feed the dispatched first responders as well as all levels of incident command.

Moreover, as RFID tags, communication, sensors, memory and processing become cheaper and with greater capacity said bracelet functionality could become common in standard wearable electronics, people could routinely use them to download their relevant previous medical history, allergies, genetic predisposition, etc. These bracelets would thus be also readily available to be used for self e-triage or e-triage by first-on-scene untrained civilians.

In yet another useful embodiment the above mentioned bracelets would enable effective search and rescue. Tracking people and assets in multistory building by RFID tags was proposed in U.S. application Ser. No. 11/868,908 by Deavilla. A further goal of the described embodiments, in certain natural disaster scenarios, like a Tsunami or a Hurricane where there is sufficient warning time, is deploying such bracelets to a scene and wearing these would become an integral part of the recommended standard of civilian preparedness.

Numerous proposals suggest how to provide high situational awareness in the aftermath of a disaster mainly by allocating cellular communication network resources to emergency response personnel or by prioritization. See e.g., U.S. application Ser. No. 11/609,216 by Gage et al., Ser. No. 12/273,146 by Smith and Ser. No. 12/423,062 by Greene et al. A goal of the described embodiments is to introduce new trust levels and application tools on phones to enable first-on-scene civilian volunteering physicians or other civilian volunteers with some relevant training to be able to contribute in the event of the disaster by using the application or by accessing special bracelet or other wearable devices. Such volunteers could also undertake special training to be eligible to assist e-triage or medical assessment.

These users would be identified by the emergency operators as trustworthy and categorized and weighted to their experience or skill level so that their field reports would be qualified and trusted by the incident command. Apart from medical triage and medical reports they would be able to assist in surveying aspects of damage sites and provide early trusted situational assessment. Additionally, bi-directional communication between them and the incident control would further assist in clarifying swiftly the situation on the ground.

A medical device inventory management system including one or more RFID tags was proposed in U.S. application Ser. No. 10/579,517 by Ortiz et al, however, does not address the wider inventory management and aid deployment opportunities of the described embodiments, enabled by the combination of first responders, applications, bracelet devices, and medical kit solutions and integration with incident command systems, data aggregation and analysis systems, as well as increased resilience through messaging, delay tolerance and mesh network approaches.

Various prior art also outlines the application of UAV (unmanned aerial vehicles) in field situations, generally in military conflict, and their role in surveillance, targeted weapon delivery, medical assistance, however, do not address some of the benefits of the described embodiments deployment approaches in large scale deployment of low cost, or light UAV systems, coordinated UAV cluster or swarm activity via a central command UAV, or combination with some of the sensor modules, deployment and drop solutions, or modular payload solutions described herein.

Despite the numerous examples of prior art in the field of disaster management, communications infrastructure and medical assistance, few address the problems outlined here or provide the benefits of the holistic and integrated approach to utilize skilled assets already caught up in the disaster, simple accessible tools, modular designed solutions, integrated e-triage approaches, communication approaches and rapid delivery systems.

SUMMARY

According to an embodiment of the description, a disaster response system includes a communication infrastructure including a plurality of sensor assemblies configured to generate data indicative of at least one of environmental conditions, motion, position, chemical detection, and medical information; and wirelessly provide the generated data to the communication infrastructure. The system also includes an incident command infrastructure configured to exchange data with the communication infrastructure; and detect an incident based on the data from the sensor assemblies. The system also includes an unmanned aerial vehicle (UAV) configured to deliver a payload in response to the detected incident.

According to another embodiment of the description, a system includes a mesh network communication infrastructure implemented by a plurality of communications modules; and a plurality of unmanned aerial vehicles (UAVs), where each of the UAVs is configured to be coupled to a deployment system. The communications modules are deployed by the deployment systems.

In accordance with embodiments of the description, there is provided a disaster response system (DRS), preferably comprising at least one of or in combination; a communication and monitoring environment (CME), modular aid solutions (MAS), deployment system (DS).

BRIEF DESCRIPTION OF THE DRAWINGS

The accompanying drawings illustrate presently preferred embodiments of the description and, together with the detailed description herein, serve to further explain the principles of the embodiments described herein.

DETAILED DESCRIPTION

Figure 1:
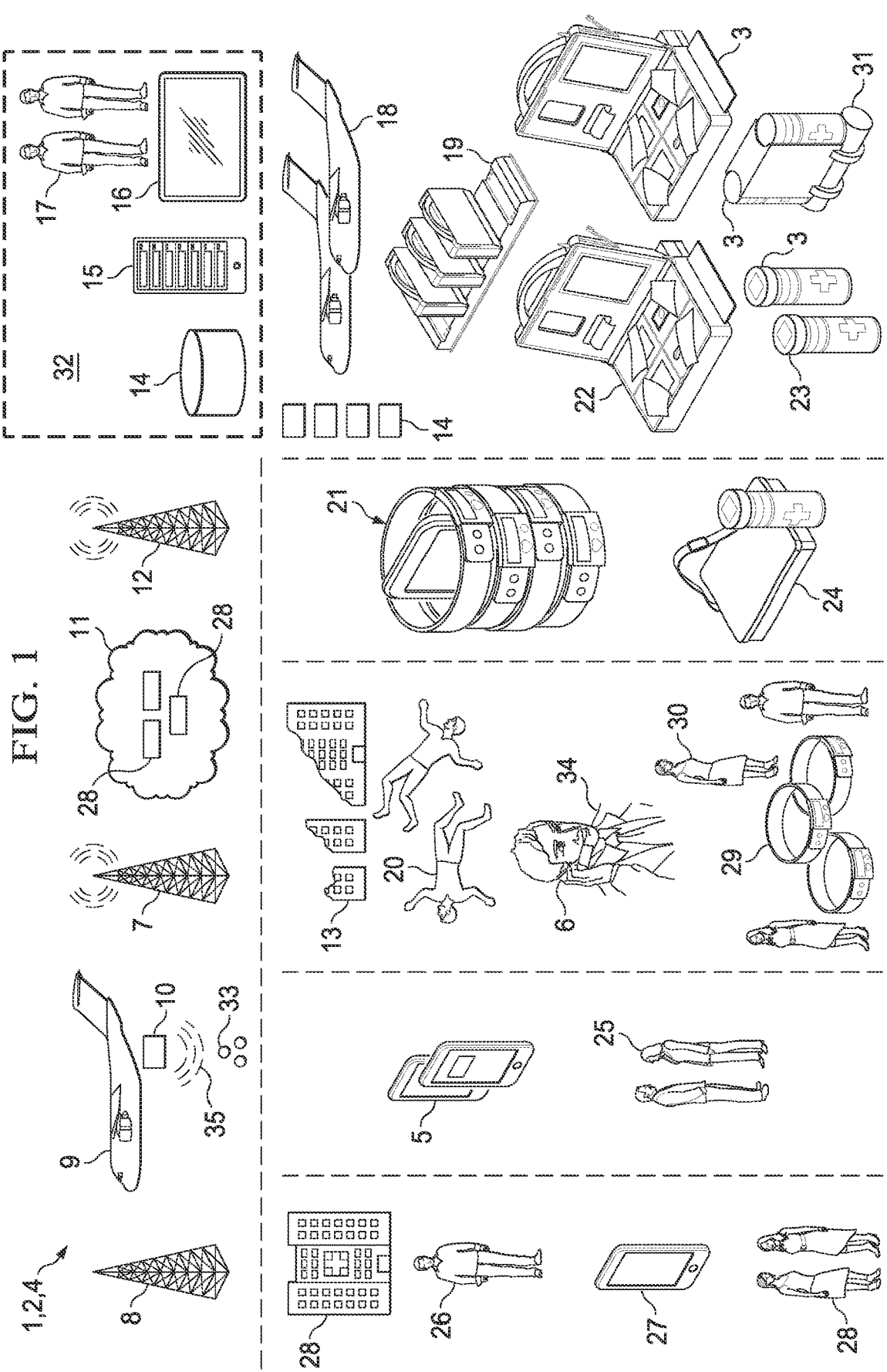
FIG. 1 illustrates a high level schematic of elements of the Disaster Response System (DRS) 1 preferably comprising at least one of or in combination a communication and monitoring environment (CME) 2, modular aid solutions (MAS) 3, deployment system 4 (DS).

In a preferred embodiment said CME may comprise a communication infrastructure such as a sensor network or cellular phone network, consisting of a plurality of sensor, wearable units or client phone devices, wireless radio communication means, back-end server and data infrastructure, and management and advice tools. Where said network and infrastructure is capable of wireless data exchange with sensor devices or wearable units, or transmitting compact 'text' SMS messages (Short message service e.g., up to 160 7-bit characters), voice or other data services to/from end client phone devices, in normal operation, or is capable of basic data transmission and exchange in reduced operation, or is capable of real-time or delayed transmission of compact priority messages when infrastructure is down or re-established during a disaster by means of a modular solution aid (MAS) communications mast, transponder or repeater, deployed to the scene via a deployment system (DS).

Said CME also preferably comprising a monitoring environment for local or user data gathering in real-time or delayed transmission, by means of a sensor on a sensor device, wearable unit or phone client device, such as a light, temperature or audio sensor, camera, scanner, MEMS (Micro-electromechanical system), chemical, biological, or motion sensor, for measuring for example an environmental property, geo-graphic location (e.g., via a GPS-global positioning system chip, or accelerometer and computation or triangulation means) or site scene data capture, or via external sensor apparatus (e.g., a medical equipment). Said phone client devices also in further embodiments capable of wireless data exchange or aggregating data messages from nearby sensors or wearable units.

Said monitoring environment data gathering also by means of a software application and memory on said sensor, wearable unit or phone client device that facilitates a sensor computation or history analysis, user preferences and security management, local data caching, or facilitates user driven new data entry, menu tree and icon selection and drill down questions or status flags.

Said sensor computation or history analysis for example being an alert computation or event detection on a step-change in performance, change pattern or reporting of a sensor as described, such as an accelerometer, or environment sensor, or a combination of a sensor history or multiple sensors. For example, a computation may detect a fall or car in motion, transport action or likely accident event by means of a change in GPS and accelerometer behavior. Similarly, a correlation of a stationary phone changing to a periodic oscillation with other periodicities in other phones or sensors, may indicate an earthquake event, and thereby a network of phones and sensors reporting data could enable a precise map of earthquake impacts across a region, and as actually experienced across different soil types and building formats. Similarly, a real-time audio sensor and correlation across a group may indicate a shooting, blast or environment sensor a pollution or other event. Similarly, aggregate and correlated GPS or device location data provides information on groupings of people as well as historic or predictable trajectories, enabling clusters of people to be identified or prioritized in the event of a disaster. Such data where locally cached also providing a form of information resource to enable a user to re-trace their steps when lost or as one evacuation choice option.

Said user preferences and security management being a means to control access to any sensor data shared dynamically with the network, such that GPS trajectory data could be hidden and unavailable in normal use, but set with a preference to release to a relative, employer or emergency service in the event of a disaster or crises event, e.g., the ability for an employer to see last location and number of employees in specific locations. Similarly said security management may be used to allow the client phone to have previously stored or receive background data, but only be able to access the data in the event of a disaster or on security key release. Said user preferences data—also providing a means to authenticate the user and trust or experience level, for example at registration or set-up. Said trust level providing to employers or external authorities the experience of qualification skill level of the user, e.g., first aid qualification or civic role (e.g., school teacher, first responder, office safety manager, community emergency response team (CERT) level) to enable any data exchange with an incident command or emergency service to be qualified by trust level for accuracy assessment or potential leverage of the resource caught up in the disaster.

Said local data caching, being a means of complementing base data stored on the device, with geo-local or disaster relevant data-updated on request or in the background when entering a new or specific zone of risk, or received by the device in advance of a predicted event or disaster risk, or updated wirelessly in proximity to a disaster data resource point (e.g., in a building), or updated at the instance of a disaster via a rapid broadcast system, or following a disaster when a network communication becomes available. Similarly, local data caching may be used to store recent sensor history or GPS data, as a form of 'black box' data track for analysis or newly entered user or gathered data, to send on request or when a communication network becomes available.

Said base data may for example include general disaster and safety advice, including emergency aid advice such as initial actions, or first aid advice and instructions. It may also include local data relating to the frequent home and office locations of the user, downloaded at registration or updated wirelessly when in that location, such as local map, key medical or emergency contact locations in the area, location of nearest medical resources (e.g., first aid kits, defibrillators in offices) or details of employer/office first aid contacts. Similarly, it could contain state information—e.g., local laws or state advice on disasters (e.g., earthquakes or hurricanes and links to notable resources—e.g., websites). For a state, civil organization or corporation using the system, said base data could be maintained as part of the back end server and data infrastructure and updated frequently.

Said pre-cached or post event geo-local or disaster relevant data or risk zone could for example include local evacuation points or routes, floor plans, local points of interest-such as medical resources or first aid points, hazardous material on site or advice on such hazards. Risk zones could include transport systems-providing transport specific safety advice (e.g., for ships, airplanes or trains), or when users undertake a risky activity (e.g., a sport or using power tools), or visit a specific site (e.g., an industrial or factory site). End client devices could automatically receive and cache such detailed local data based on geo-tag information shared with the back-end server, and pre-stored in the background, and then deleted after a period of time, or after leaving the zone. Detailed information-such as full floor plans or hazardous materials could also be encrypted via security keys, and only released via a security key or key trigger issued in the event of a disaster or local alarm release. Said local alarm preferably having a means of sending a signal to the back-end server to enable a broadcast release of a security key, data or link to disaster data resource points. Similarly, in further embodiments such site specific data could be stored and cached on any phone but only made available to qualified resources at a certain level, or password security key access (e.g., professional emergency response).

Site specific data could also be stored in a disaster data resource point (e.g., secure SD data card or USB drive) in a building capable of being accessed from a distance via a wireless or radio connection by a secure reader held by local emergency crews, which would be especially valuable in the case of hazardous materials on site, and could become a suggested legislated requirement. Said data resource points could also in further embodiments keep a real-time monitor and count of all personnel in the facility as a form of building 'black box' to aid emergency resources in the event of a mass casualty or collapse event.

Said base data and pre-cached local information, or building disaster resource points, having significant benefit in the event of a disaster when networks are unavailable or overloaded, as end client phone devices could be used as a resource and evacuation aid, having appropriate immediate map, evacuation and point of interest data.

Said data exchange being in preferred embodiments, mediated by means of a disaster messaging standard (DMS) capable of coding and compressing key information and data resources into short messages or data packets capable of being sent via SMS or other emergency exchange protocols, such that pre-cached local information such as evacuation maps or points of interest, can be exchanged efficiently with delay tolerance at low data rate and bandwidth, and requiring minimal battery and processing use, to enable data to be cached effectively. Similarly, in the event of a disaster, concise additional information can be broadcast or downloaded to phones containing key data without absorbing valuable high data network communication. Said disaster messaging standard (DMS) capable of being visualized rapidly via a Disaster Markup Language (DML) so that key features, e.g., points of interest of evacuation on a map, could be sent efficiently and layered onto an existing local map co-ordinates in an analogous way to a mapping keyhole markup language (KML), or used as an extendable mark-up language (XML) to tag and parse data from one disaster storage form and share with other resources or form disaster resource ontologies. Said DMS and DML formats enabling a greater enquiry, compatibility and exchange of data between disaster systems.

Said software application preferably being usable for user driven data entry and selection using a series of menus, icon selection and drill down questions and status flags, to simplify user data entry, ensure consistency in disaster data categorization and facilitating coding into a disaster messaging standard (DMS). Said categorization for example could utilize application version number, menu layer, option, and flag result, to compress complex information into a short form string, that could be transmitted and allow classification at the back-end server and data infrastructure level, expansion and visualization via a similar mark-up language, automatic clustering and prioritization.

Such user driven data entry could in preferred embodiments include a menu and icon driven approach to enable users to provide reports on an incident or disaster, including classifying type and scale of disaster, assessing number of victims or casualties in need of assistance, or prioritizing request for resources and assistance. Similarly said end phone clients could capture photographs, audio, text commentary or other sensor data from the site, and transmit the data or process to report at a meta-tag level key parameters, such as photo time, location, direction, classification type for transmittal via a DMS string, or to be sent on demand should bandwidth become available or if the remote system releases an authorization to send a larger data file. Such an authorization could form a release sequence header on the string or SMS to determine a transmission priority, where said CME network infrastructure provides transmission access or priority to such messages. Similarly, in a further embodiment of a deployment system comprising an unmanned aerial vehicle equipped with local communications mast/transponder module, said devices could accept such larger data messages with sequence headers, and relay them via an uplink, mesh network or satellite system, as an alternative to such messages being sent via the damaged communications infrastructure.

In a preferred embodiment, such a user driven data entry system could be applied to assist disaster site medical triage, by enabling semi-qualified people or semi qualified personnel who are caught up in a disaster site to use the software application on a phone client device to provide site reports and medical assessment of casualties, to describe and prioritize those in need of the most urgent medical assistance or for which limited medical resources would have the greatest impact or likelihood in saving or preserving life. Such decisions are complex, emotional and require accurate field data, to allow incident command to assess how best to deploy often limited or time delayed medical resources, personnel and medical aid to the field. Said trust level of the user, together with structured menus, and use of DMS transmission codes, allow data to be aggregated and scored by qualification level, to aid incident command decisions and victim number and location assessment. First professional responders arriving on the scene could then also utilize similar tools on phone client or PDA devices to make and report further triage assessments or of large groups of people at evacuation sites, or refugee camps, to prioritize the need for medical assistance. Such prioritization is likely to be critical in the large scale disasters such as earthquakes described earlier.

In a preferred embodiment, electronic information bracelets or other wearable devices could assist the process of electronic triage, where said bracelets are carried or placed on people or casualties caught up in the disaster, to aid tracking of their location, tagging electronic data-such as triage level, medical assessment, name or medical details (e.g., blood type, diabetes, allergies), and avoid duplicated assessment or double counting of victims observed by other parties. Said bracelets typically comprising a low power and low cost form of short range communication such as RFID, Zigbee, Bluetooth, a machine readable memory, an optional power unit (such as a coin battery cell, or power paper strip), a low energy display such as liquid crystal, OLED or LED, affixing means-such as a strap capable of secure attachment to the wrist or leg in a manner to preferably prevent easy removal by the user, a means of attaching or affixing a printed label or record. In a further embodiment said bracelet could support more advanced communication, such as a two-way text data exchange or low cost phone module, could be coated with an electroluminescent material or a piezo-luminescent material capable of light generation with motion, or include more automatic vital signs monitoring means such as means to measure blood rate or pulse rate of the wearer by means of sensors or wires within the strap or a cuffless device, or detection of skin capacitance variance, or respiratory rate via impedance measurement, or through connectivity with other implantable (pacemaker/defibrillator, HR monitor, BP monitor).

Said bracelet capable of exchanging and synchronizing data with a nearby phone device, medical PDA or intelligent medical kit unit, or wirelessly with a UAV (unmanned aerial vehicle) or communications mast/transponder deployed to the field, or in further embodiments to form a mesh network with other bracelets for information exchange. Said bracelet also capable of storing critical patient medical record details (such as blood type, allergies, medical treatments) preferably as a DMS message format.

Said phone application, Medical PDA or bracelet capable of showing and storing in machine readable or user visual form, traditional triage category nomenclature (CDC) priorities of Priority I Red: Immediate (e.g., controllable massive bleeding, tension pneumothorax), Priority II Yellow: Delayed (e.g., simple but significant fracture-femur, hip and humerus), Priority III Green: Minor (e.g., abrasions, contusions, sprains, simple lacerations, walking wounded), Diseased/Expectant patient-Black (minimal chance of survival, e.g., massive head injuries, >95% 3rd degree burns).

In a preferred embodiment, said medical triage and assessment could be aided by a first aid diagnostic kit comprising basic first aid materials (such as plasters, bandages, scissors, anti-septic patches) and a plurality of diagnostic tools, such as a for HR EKG/ECG (electro-cardiography), Oximetry, pulse and blood pressure monitor, USB ultrasound. Said diagnostic kit being preferably comprised of a satchel like pouch containing first aid materials and a cylindrical electronic triage pouch containing a plurality of electronic triage bracelets. Said bracelets could be wrapped around a smartphone when deployed as stand-alone of shippable unit. Said kit could be purchased or available to qualified users of the phone software application, or stored in cars, homes or office first aid locations. Said first aid diagnostic kit or electronic triage pouch could also be packed within a compact capsule suitable for deployment to the scene, by means of a UAV or localized air-drop, pre-deployed e.g., in vending machines, or available at mass retail locations. Said software application storing data on nearest location of said kits, by means of the local caching and DMS message exchange, enabling the user to find nearest medical aid resources by means of menu selection.

Said software application containing suitable menus and workflows to facilitate the capture of data recorded via said plurality of diagnostic tools, and optional help pages to aid instruction should procedures be less familiar to the operator. Said software application could also aid automatic monitoring and recording of nearby bracelets (to track respiratory rate, blood pressure) or connect with implantables, as well as access patient medical data.

In a preferred embodiment professional first responders would be dispatched to the main disaster sites with an appropriate intelligent medical kit. Said intelligent medical kit preferably being formed as a series of modules and back-bone capable of rapid configuration for a disaster site or type, or extension and tailoring based on the gathered triage and medical data on needs and volumes of casualties at specific sites e.g., via DMS messages sent from phone software applications or read from nearby electronic bracelets. Said intelligent medical kit, also preferably being designed in an overall modular form, capable of being deployed to a site by means of a UAV or directed air-drop means, carried or worn on the person.

Said intelligent medical kit capable of interacting with said electronic bracelets and e-triage data in order to prioritize and guide first aid and medical assistance, update patient bracelets with new diagnostics, treatments or aid required, communicate with back-end systems and electronic medical records (EMR) and overall casualty management systems The medical kit preferably comprising a computing device, docking point for a rugged PDA with medical tools (such as diagnostic advice, medical calculator, pulse timers, prescriptions/dosage assessment), slave low energy display screen such as an e-ink material (used for example to display records or field victim management software), wireless radio communication, extendable processing capability (e.g., a re-configurable XMOS reprogrammable processor), battery power back and renewable power solutions, voltage convertors and USB hub for data/power connectivity, lighting solutions such as portable LED or OLED light panels, basic telemedicine support, RFID link with patients RFID or short range communication bracelets, RFID tags on devices and RFID reader and built-in inventory management software, tagged tools such as EKG, blood pressure and USB based diagnostic devices (such as 12.5 Mhz ultrasound, or EKG card), AED (Automatic External Defibrillator) and disposables (bandages, drugs, fluids, tourniquets, splinters, etc.). In an embodiment RFID tagging would enable software to track device and resource use, to help determine resupply needs and provide real-time field data to incident command on types of injuries treated, disposables consumed and requirements. Moreover, this platform would allow automatic management of the warehouse as well as rapid automatic packaging of specialties according to a specific disaster and its characteristic requirements, e.g., fluids, intraosseous infusion kits and vacuum splinters for deployment in an earthquake, or other specialty packs. Similarly, RFID tagging could prompt suitable advice pages to appear on a screen to assist on diagnosis, or provide learning videos/education. Said diagnosis screens could prompt a series of associated questions, checks or other relevant medical history information. For large scale refugee or pandemic disasters, further embodiments could support additional specialist packs such as SNP, DNA arrays or lab on chip readers, for assisting viral or blood assessment, to identify viruses, blood poisoning or other genetic disorders. Similarly said intelligent medical kit in future embodiments could support modules, tools such as guided an intratracheal intubation ambuaScope, automatic intraosseus line, wireless therapeutic US and enhanced telemedicine, guided thoracotomy, peritoneal lavage or advanced medical materials; powdered blood, powdered platelets, regenerative skin, biological glues, respirocytes.

Said PDA being used as an overall control interface, UI to select and control information or connect with devices or display information on the separate display screen. Said PDA accessing a similar software application to the client side phone to enable more detailed diagnostic and e-triage or accessing of bracelet patient information, or in further embodiments containing dedicated sensors and diagnostic devices. Said PDA when mounted in the docking point being chargeable by means of the USB hub and power back, said USB hub also providing power and data connectivity to a plurality of modular devices and tools or separate back-up power packs suitable for said devices, torches or accessories. Said USB hub also connected to a memory such as a SD card, which may preferably be customized prior to dispatch to a field site to appropriate disaster type data.

Said power-back preferably comprising at least two independent lithium or other battery cells, such that one battery can be used whilst the other is being charged. Said charging means including renewable solutions such as flexible photovoltaic panels used on the external surface of the medical kit, or as a separate un-foldable unit, or via an accessory mechanical charging device. Said overall power-back being connectable to a charging station rack for powering multiple batteries during storage or deployment, e.g., during air or container dispatch to a disaster site, so that power-backs can arrive topped up and ready for use.

Said overall intelligent medical kit, having a modular construction, so that sub-kits such as disposables can be easily loaded and replaced, or new tools added and placed in appropriate docking points easily by manual or automated (e.g., warehouse conveyors or simple robotic systems). Said overall modular construction also favoring attachment of deployment layer means, such as directional parachutes, or stacking onto containers for mass deployment, or for attaching to a UAV deployment platform and drop frame as part of a deployment system (DS).

Said modular construction also being standardized to facilitate a plurality of other modular aid solutions (MAS) capable of being delivered by suitable deployment systems. Said solutions could for example include an Energy generating module such as photovoltaic, fuel based, hydro or mechanical, a habitat in a box, such as tent forms, or rapid assembly shelters suitable for use as medical clinics or habitats, communications modules-suitable for recreating mobile phone transponders or satellite connectivity, or local mesh network hub support.

Further embodiments may include sensor modules suitable for assisting specific disaster scenarios for site assessment such as HD video and wireless connectivity to heldheld PDA displays, infrared scanning to identify heat sources or bodies within a space or at night, environmental sensors to measure water properties, chemical or other hazard properties, water toxins or pollutants, vegetation density and flammability. In the case of large-scale disasters in an urban area, such sensors in preferred embodiments could be attached to UAV (unmanned aerial vehicles) which could be controlled from a remote site or support onboard auto-pilot or GPS aided navigation means to navigate a path or flight plan over a disaster site, or fly or hover between building structures, or explore within buildings or cavities (or enabled by small ground or portable remote vehicles and sensor devices). Such sensor platforms could work as clusters of devices to improve coverage time, or allow greater resolution of sensor coverage.

In preferred embodiments clusters or swarms of UAVs could be locally controlled by means of a central UAV which supports more advanced navigation or remote control means, and support local wireless communication for navigating/controlling a swarm of nearby devices. Such an embodiment would have the benefit that 'slave' UAVs could be at a substantially lower price point or in certain circumstances be disposable or single-use devices, and thereby support coverage across a wide region, or ability to carry multiple payloads. Said UAVs could also be used to rapidly locate personnel within a disaster site, such as personnel wearing said electronic bracelets, or carrying end client phone devices, and also support local mesh networking and communications relay support or data exchange with bracelets and phone devices. Said devices also preferably being able to aid phone device location through being able to create local triangulation references to measure signal strength. Said approaches could similarly be used by ground or sea based ROVs (Remote Operated Vehicles), which could similarly be utilized as deployment systems for delivering aid solutions.

In further embodiments, deployment systems and modular aid solutions could include robotic platforms, capable of delivering assistance within a field situation-such as lifting or cutting heavy objects, or reaching extreme/difficult locations (e.g., in mountainous terrain, or damaged skyscrapers). Said devices may be capable of aiding forest fire reduction, building repair/stability or repairing flood defense systems or assembling sand-bags or other defensive measures. Similarly, miniature robotic systems or robotic snakes could be deployed to facilitate search and rescue or delivery of aid to casualties in a building collapse or inaccessible area, where for example a robotic system could deliver emergency intravenous liquids, injections and medicine, and establish communications with casualties for the purpose of advice, triage assessment and comfort.

In further embodiments, where said deployment layers could include parachute forms made from a thermally insulating foil material so that they could be re-used in the field for body warmth. Said foil chute could be contained in small modules affixed for example to a first aid electronic bracelet canister. In other deployment approaches, small inflatable units could be inflated by a gas unit or by a deployment layer apparatus, and allow small modular aid solutions to be dropped close to the ground such that the inflatable protects the landing, or acts as a floatation aid. In a preferred embodiment a UAV deployment platform containing a deployment layer and plurality of bracelet/mini first aid packs and inflatable's/foil chutes could follow a planned trajectory and identify casualties on the ground (or via the assistance of a remote control map link and selection means on a phone application or rugged PDA by a first responder), and drop small parcels of aid to individuals. Such an approach could facilitate rapid initial response of trackers, e-triage monitoring bracelets and basic aid to victims across a wide disaster site, or to inaccessible sites, such as house roofs in a flood scenario.

Said UAV deployment systems for disaster sensors, medical aid and e-bracelet sensors, being preferably pre-deployed to warehouses (such as FEMA locations) or other sites near areas at higher risk of disasters, such as earthquake zones (e.g., San Andreas/Bay Area), or hurricane zones, or storing remote operating vehicles in sea vessels within range of tsunami risk sites, to facilitate the speed of response in the event of a disaster. Similarly, larger scale deployment platforms could use high-altitude air platforms, blimps or dirigibles, or space platforms such as low earth orbit satellites in support of communication modules, such as transponders or repeaters, or sensor modules, such as HD cameras and Infra-red, or in combination with a plurality of platforms of UAVs for synthetic aperture radar sensing technologies, or for storage of low weight aid systems, such as e-bracelets or other aid solutions. In the event of large scale heighten crises, requiring rapid response, civilian airplane fleet could also include solution modules capable of being deployed in flight, and in future, space systems could support the ability to drop a module to anywhere on earth within 45 minutes of a disaster, to provide a local communications module or other solution aid.

Deployment systems may also preferably include local flight control means, such as a local Air Traffic Control system for UAV movements, to be able to ensure UAVs deployed in a civilian area (pre disaster/air space restrictions) are tracked, reported and coordinated to avoid conflicts within the air-space with civilian or military air systems, or other air users. Such systems could be deployed as solution modules, for example comprising a deployable portable radar system (such as those made by Raytheon) which could be dropped to a site by means of an air drop and directed parachute, in combination with local 50-75 m radius air control systems, as proposed by SAVDS. Such an approach as part of said deployment system would enable a rapid deployment and authorization to use UAV platforms in the event of a disaster, at standards close to those expected by air authorities such as FAA. Similar use of said platforms could enable local operations to be established in remote, conflict or politically sensitive areas of operation, where data and local air information could be made available, or controlled by local government or military resources, whilst still providing common data standards such as DMS to enable data interaction. Said systems could also in preferred environments support fire-walls, or other security means, or keep isolated or in country of origin, technologies, such as flight control or autopilot means, that have restrictions on technology transfer.

Similarly, in the event of certain disaster risks, e.g., forest fires, ballistic systems could be used to dispatch solution modules or micro-UAV systems rapidly to a fire site, to aid sensing, evacuation or local incident response.

Risk assessment of potential disaster sites could help pre-deployment of modular aid solutions and UAV/ROV platforms, including identifying suitable big box retailers that could carry medical aid kits as commercial items, with live inventory visibility and RFID tagging to enable rapid pre-authorized distribution of collection in the event of disasters. Post event analysis, of behavioral patterns of e-triage, tracking/tagging maps of victims, recovery rates, and evacuation rates would in preferred embodiments create substantial data mines held within the back-end data infrastructure enabling better forecasting and prioritization for future disasters. Similarly, early tremor analysis, provided by geo-tagging and mapping correlative phone accelerometer vibrations, could enable improved forecasting of subsequent larger earth quake events. Such data could be locally cached on phones and shared as a form of background distributed sensor network reporting tool, to contribute to safety research as a virally adopted program, e.g., when phones are left in charge docking stations. Such an approach could also be used to send DMS messages to critical infrastructure to shut down machinery, transport systems, or electricity/gas infrastructure within the first few moments of a major quake or disaster event, potentially protecting significant resources from increased damages. Similarly, such rapid messaging approaches could pause traffic lights, or be a trigger in releasing phone application locks, or raising the alert or preparedness status, or raising the threshold/volume of local caching of data in advance of a disaster likelihood.

Said incident control and backend management systems could therefore maintain a permanent presence and control and aggregate significant data feeds, from worldwide sensor networks, satellite and space monitoring and image systems, data feeds such as consumer behaviors or social networks, such as Twitter, or phone activities, in order to perform complex behavioral modeling, fusion modeling, cluster analysis and rapid neural network or Artificially intelligent pattern recognition to identify trends of patterns. Such techniques have already been indicated for pandemic spotting, but could be used more extensively with the benefits of the medical and triage embodiments in providing significantly increased access to qualified data.

Visualization means in preferred embodiments can further aid rapid analysis and decision support, such as algorithmic clustering via a algorithms weighted by trust level, population impact, number of incidents. Back end software and data infrastructure preferably including command can control systems to support decision making, analysis of incoming DMS messages and reports from phone client software applications, triage data, and enable incident managers to control advice, evacuation and guidance advice to sub-populations of software application users, to over-ride of complement default settings and evacuation data stored in local caches. In preferred embodiments incident managers could view a visualization of disaster zone, major evacuation paths, and select proportions to be directed to different paths (e.g., bridges, major roads), and authorize targeting or of specific advice messages at different times to sub-clusters of end devices, or be assisted by algorithmic means in calculating optimal paths by considering person or vehicle density, behavioral models, disaster site information/obstacles, and formulae, for example geo-tag triangulation analysis and sending messages to ensure safe dispersal to nearest or optimal guided paths. Such systems could also be applied in large scale civilian sporting or other events to aid modeling, mapping of arrival and dispersal of crowds and spectators. Various real-time, post-event analysis could aid in the development of optimal guidance and evacuation ontologies, in response to different disaster scenarios, and rapid forecasting (e.g., of fire spread or weather patterns impacting toxic gas or other dangerous substance) dispersals could further aid and adapt real-time guidance maps.

Referring to FIG. 1, overall CME 2 is shown as example to include a back end data 14 and server 15 infrastructure with visualization systems 16 and incident managers 17 forming an overall incident command infrastructure 32, radio mast or transponders 12, a physical or wireless network 11, sensors 33, reduced service mast 7, inoperable masts or transponders 8, UAV platform 9 carrying a payload 10 which indicated as a temporary communications unit broadcasting a signal 35, wearable bracelets 29, phone client units 5, 27, 6 in the disaster site which is indicated with intact buildings 28 and damaged or collapsed structures 13; modular aid solutions 3 are shown as example to include field resources such as portable first aid kits 24, electronic triage bracelet and Phone packs 21, and warehouse or response modules such as intelligent medical kits 22, and portable carrying apparatus 31, droppable first aid canisters 23, charging and packing stations 19, sensor modules 14; deployment system 4 is shown as example to include deployment UAV platforms 18, sensor carrying platforms 9 which may preferably support loading and deployment layers and chutes. Where for example people 26, 25, 28, 20, 30, 34 are caught up in disaster site. In an example scenario civilians 25 have access to a phone client unit 5 which has connectivity to the network 11 via a semi-operable communications unit 7 or a temporary UAV platform 18, where said phone client unit 5 is shown receiving a compact DMS message 28 providing updated evacuation advice. In another scenario civilian 26 is shown with access to a phone client unit 27 which has no live connectivity but can still access basic evacuation data and advice that had been previously cached locally in the device memory before the incident took place, or on a delay tolerance when passing through an area of live communications, and is also able to direct/advise other groups of people 28 without phone client units 27. In another scenario there is a shown a collapsed structure 13 with casualties 20 in proximity to the building, and a further person 34 with access to a phone client 6 where said person 34 is a semi-qualified or professional resource with some medical knowledge who is able to use the software application to assess and report on the disaster site 13 and use the device to assist in the process of electronic triage of the casualties 20, where preferably said person 34, also has proximity to a basic first aid kit 24 containing electronic bracelets 21, 29, or is directed by the phone application to a nearby first aid kit (e.g., in an office or vehicle) and can use the kit and electronic bracelets 21,29 to aid in the assessment of casualties, where other persons 30, have similar access to a supply of electronic bracelets (e.g., via an air drop or UAV 18 delivery), or have already been assessed.

Figure 2:
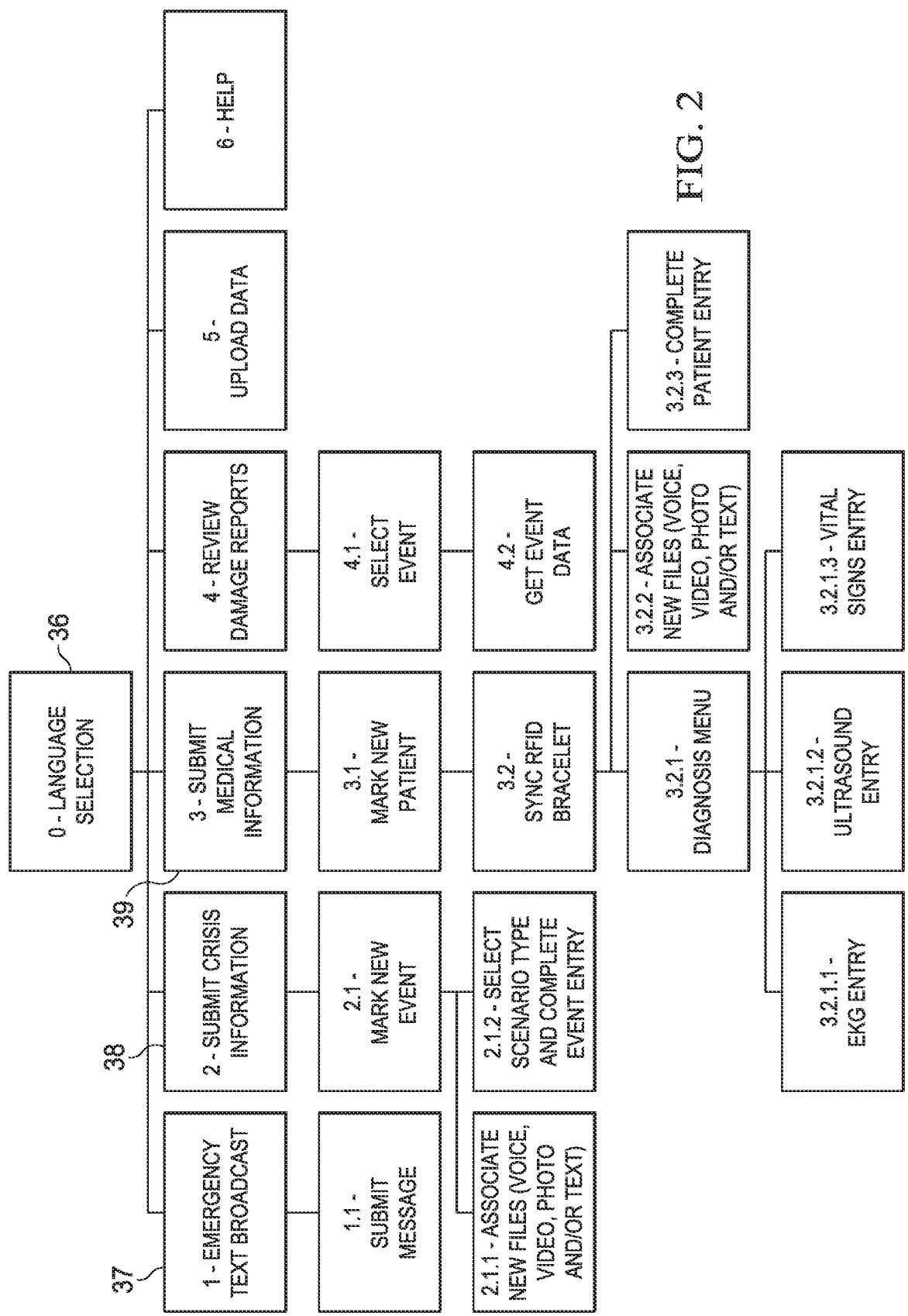
FIG. 2 shows a schematic of a User interface and window function flow 26 for an example software application for running on a phone client device 5.

FIG. 2 shows a schematic of a User interface and window function flow 26 for an example software application for running on a phone client device 5, where example menu option 37 provides a means of a user sending an emergency priority message using the compact DMS message 28, example menu option 38 provides a means for submitting a crises report, such as categorization, photographs, recordings and description of a damaged site, which would be geo-tagged and compressed for key data into a similar DMS message 28, or sent with media if bandwidth is available or on request along with a trust level identified by the user type registration enabling incident command 32 to analyze and qualify the information, example menu 39 provides a further reporting example for assessing medical needs, at the patient or group level, and entering initial diagnostic or triage assessment to create a patient record and preferably also in combination with an electronic bracelet 29.

Figure 3:
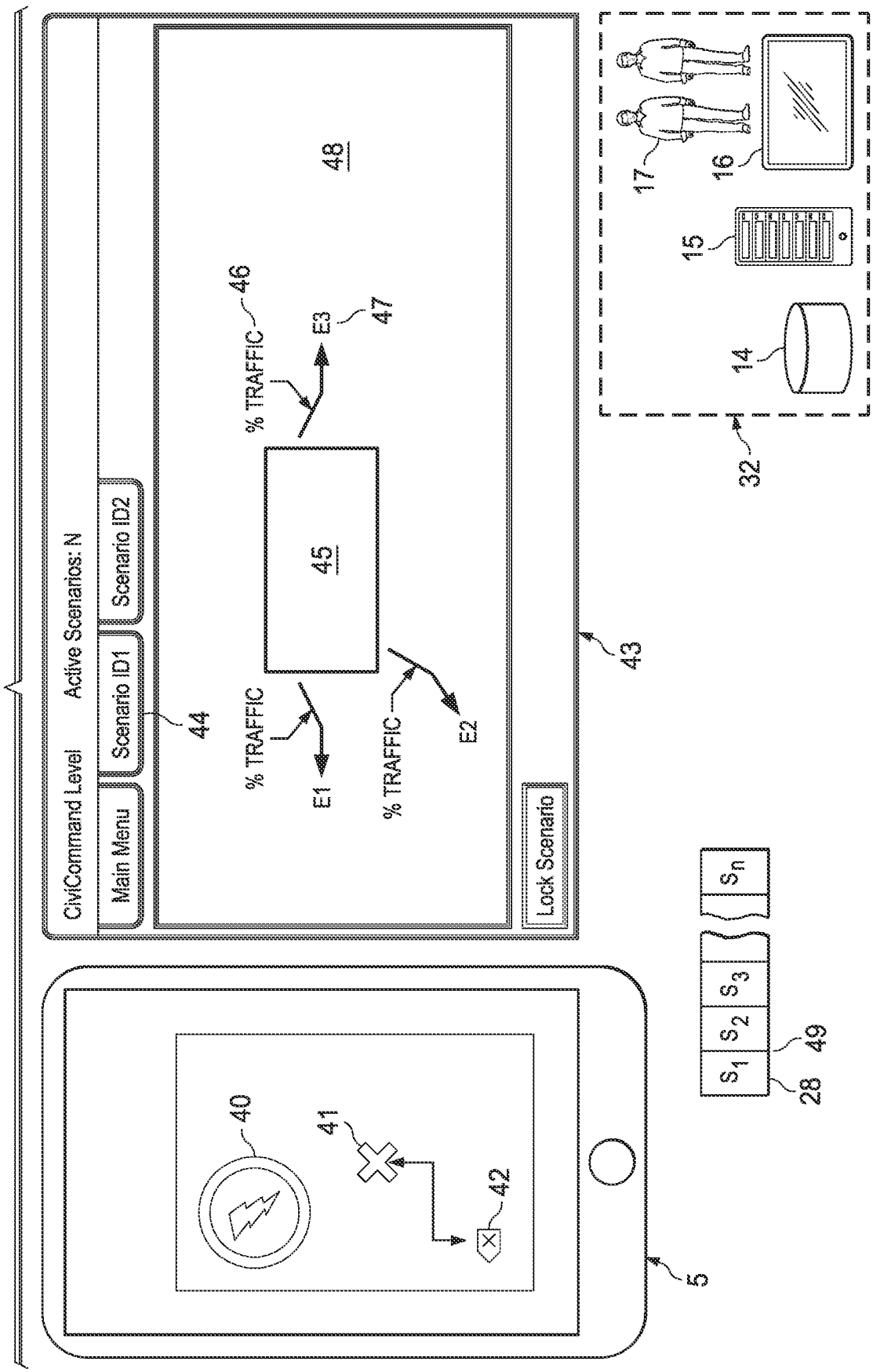
FIG. 3 shows a further schematic of a phone client device 5 running a software application displaying an example evacuation map 40, and suggested route 41 to an evacuation path or safe cluster area 42.

FIG. 3 shows a further schematic of a phone client device 5 running a software application displaying an example evacuation map 40, and suggested route 41 to an evacuation path or safe cluster area 42, where said path may be calculated on the software application on receipt of a DMS message alert 28, containing hazard and evacuation geo-tag information, or calculated from a recently cached local points of interest data message in the absence of a real-time communication network, and said DMS message preferably encoding data into a preferred DML mark-up data string 49 of key mapping features. The back-end data and server infrastructure at incident command 32, is also shown, whereby operators 17 may use a visualization system 16 to display a command control application 43, capable of showing an incident map 48 stored on a local database 14, and highlighting the risk or disaster site area 45 and using algorithmic and analysis means on said server 15, to calculate preferred evacuation routes 46, 47 based on numerous factors including an assessment of data reports from the field sent by end phone client device users, population analysis of mobile phone density or other data aggregation means or from user assisted instructions such as preferably using a multi-touch user interface where incident operators 17 can draw or outline evacuation routes. On confirming a preferred route and selecting, in this example, traffic percentages 46, the system would calculate and send geo-targeted DMS 28 messages to appropriate sub-groups within or near the disaster site 45, to provide appropriate geo-locally specific advice and guided evacuation to personnel and civilians in the field.

Figure 4:
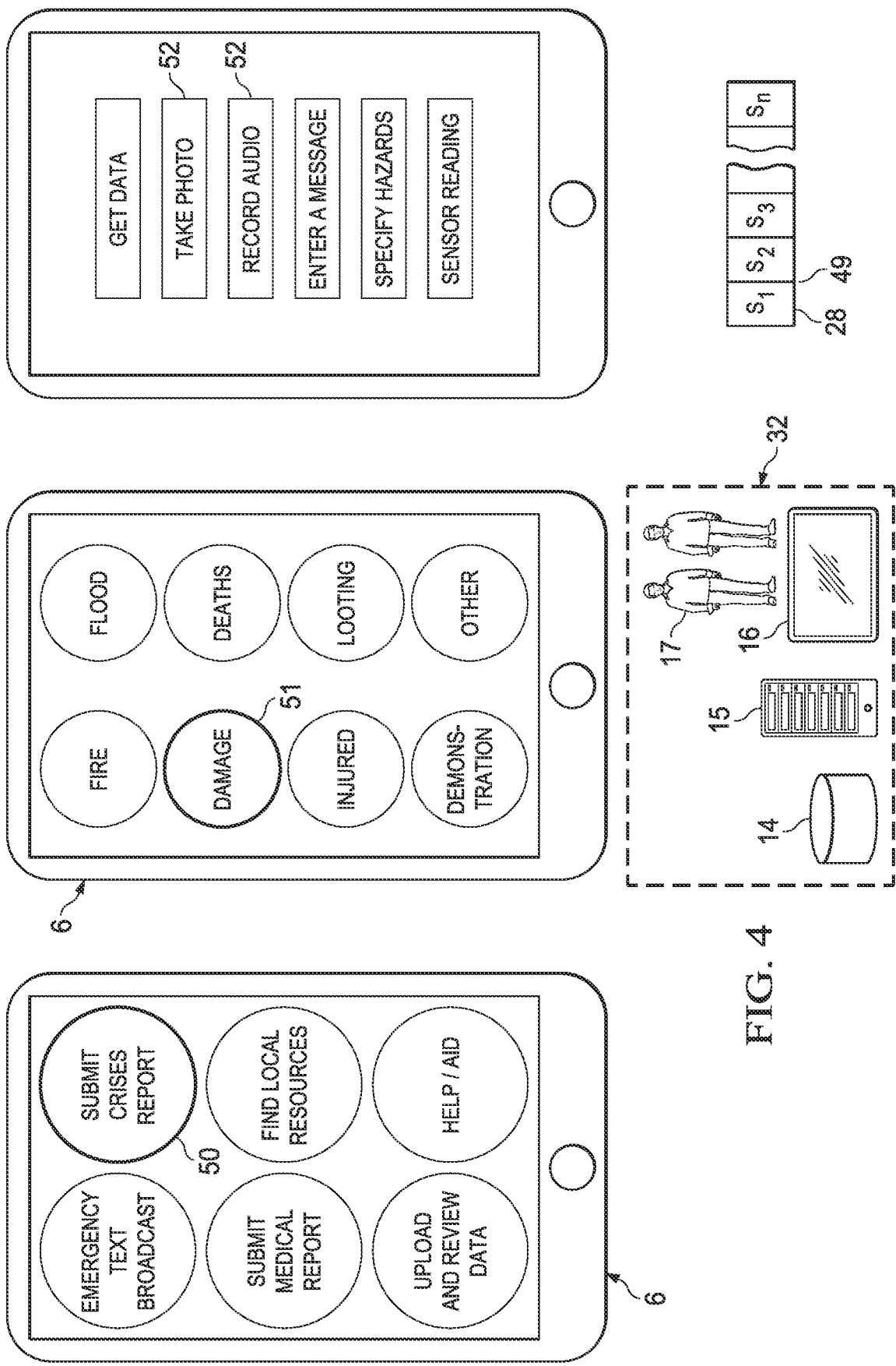
FIG. 4 shows an example schematic of a client phone device 6 being used to facilitate the qualified reporting of a disaster site using menu selections 50 and categorizing via tiered menu icons 51.

FIG. 4 shows an example schematic of a client phone device 6 being used to facilitate the qualified reporting of a disaster site using menu selections 50 and categorizing via tiered menu icons 51, and entering user data or using the device to capture local data 52 via embedded sensors or recording means, and then converting into DMS messages 28, comprised of coded strings 49 to be sent as short messages over a delay tolerant network. Said messages 28 being received by incident command 32 and categorized to aid operators 17 and systems 15 in rapidly assessing site damages to aid prioritization. Said software application being similarly used for reporting casualty or other victim electronic triage assessments.

Figure 5:
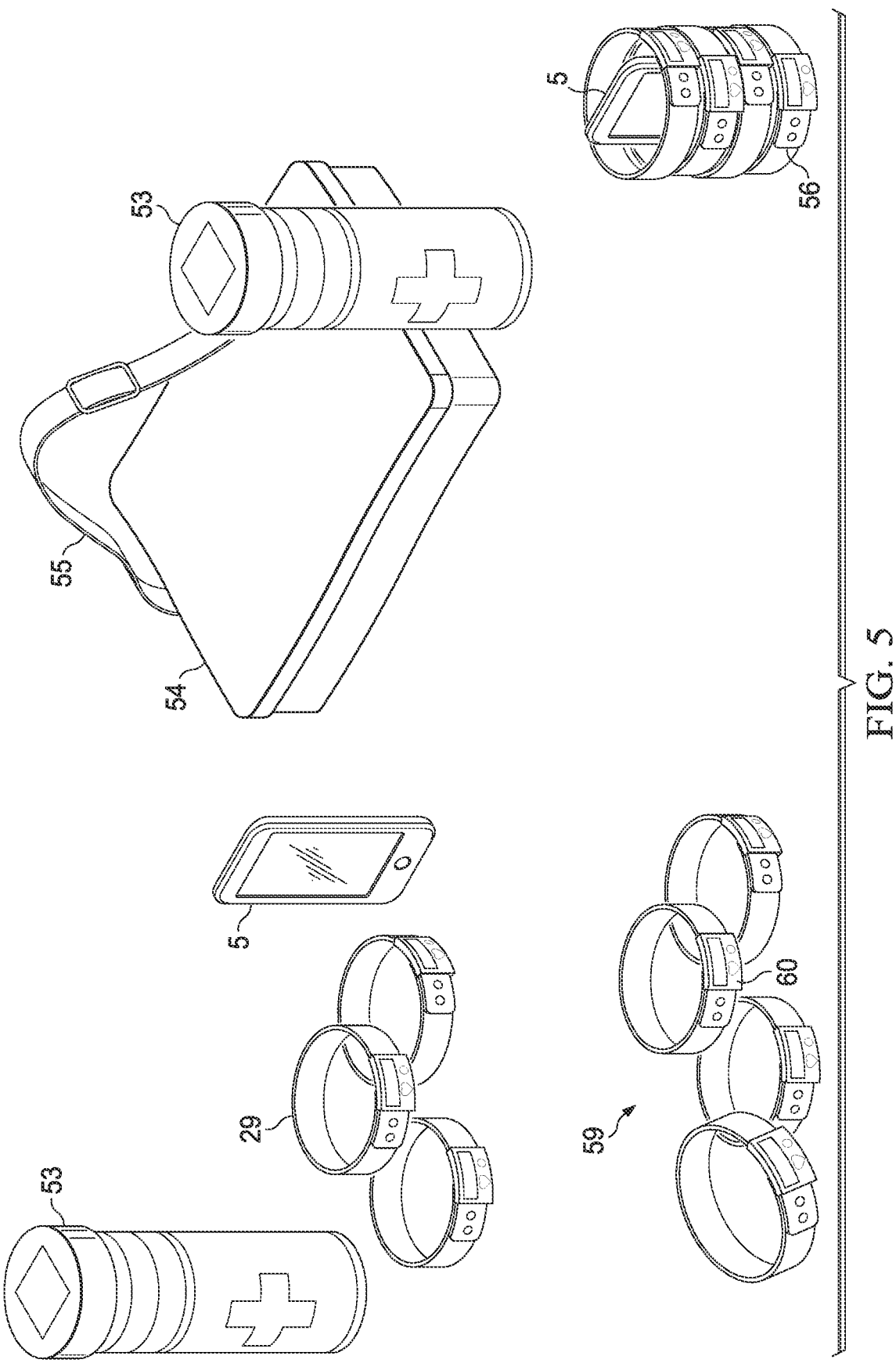
FIG. 5 shows example first aid capsule 53 and kit 54 (as modular aid solution 3) that could be rapidly deployed to the scene by deployment systems.

FIG. 5 shows example first aid capsule 53 and kit 54 (as modular aid solution 3) that could be rapidly deployed to the scene by deployment systems, such as UAV (e.g., 18) or targeted air-drops, or available within the disaster site, at offices, medical centers, big-box retail stores, or pre-deployed in vending machines, or available to qualified resources in vehicles or other locations. Said capsule 53 preferably comprising a droppable canister containing a plurality of electronic triage bracelets 29 and phone client unit 5. Said capsule 53 in a further embodiment may be the approximate size and form of a beer can, and capable of being stored in a vending machine. Said capsule 53 being preferably reversibly attachable to a first aid kit 54 containing basic disposable and diagnostic resources as described herein, where said kit 54 can also preferably be carried on the person such as via a strap 55 or easily attached to a deployment layer (such as a parachute, or inflatable) where dropped into a field. Said plurality of electronic bracelets 59, being used to rapidly assess and electronically score and tag casualties in a disaster site by using the phone client device 5, and said bracelets 59 possessing a face 60 to show a visual record of an electronic triage assessment or vital signs measurement, together with data storage, alert and communication means.

Figure 6:
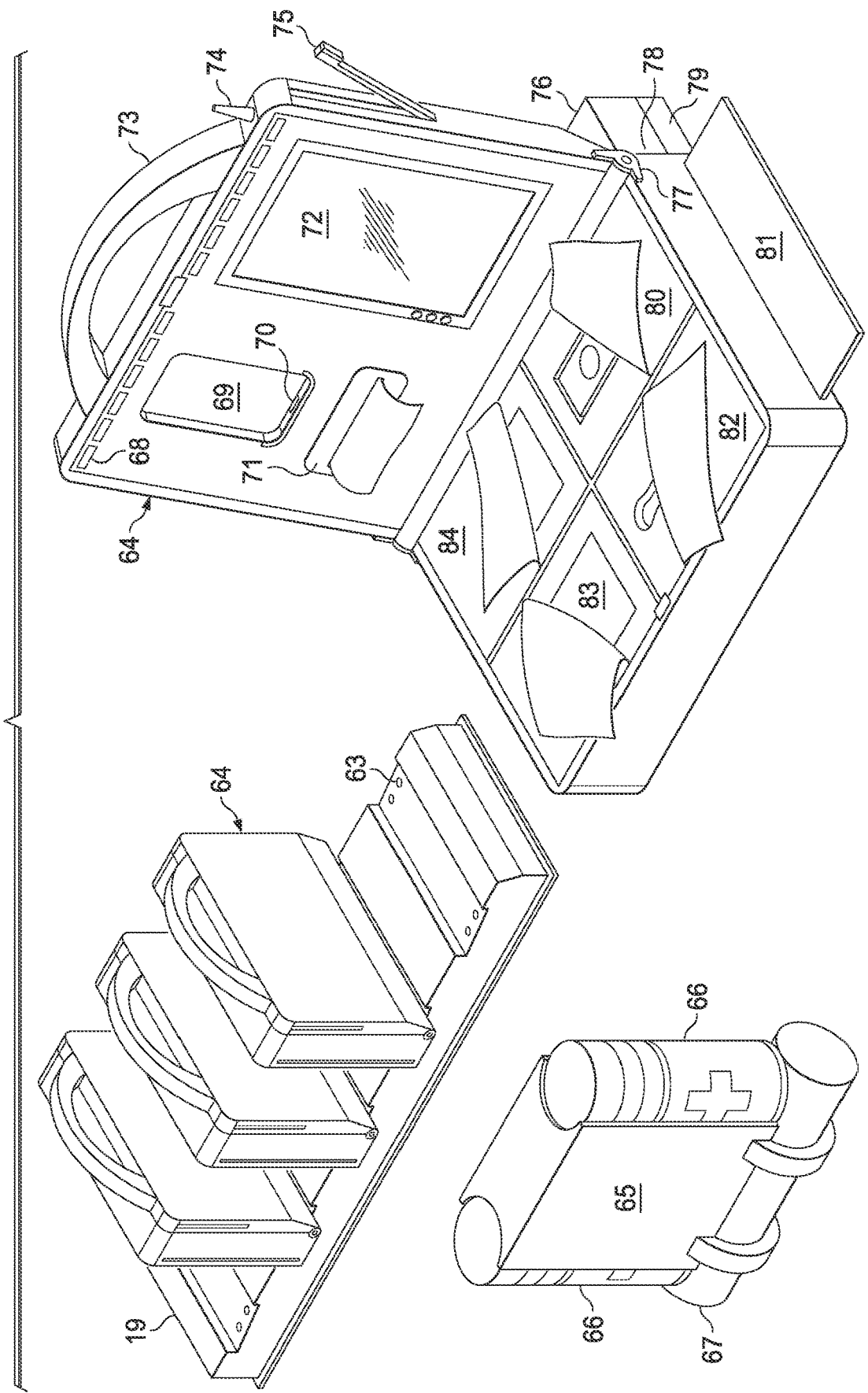
FIG. 6 shows an example of a modular aid solution (3) being an intelligent medical kit 64 capable of being worn on the person by means of an outer case 65 capable of also attaching specialist modules such as resuscitation 66 or specialist disposables such as orthopedic vacuum splinters 67.

FIG. 6 shows an example of a modular aid solution (3) being an intelligent medical kit 64 capable of being worn on the person by means of an outer case 65 capable of also attaching specialist modules such as resuscitation 66 or specialist disposables such as orthopedic vacuum splinters 67. Said intelligent medical kit 64 shown as comprising background OLED lighting 68, docking point 69 for a detachable rugged PDA or smart-phone 5 (not shown), phone charger contact 70, label printer 71, slave OLED or e-Ink low power screen 72 (suitable for showing patient records, diagnostic advice or learning), a carrying handle 73, wireless radio antenna 74 (suitable for also creating a local hot-spot/network), super-bright LED torch and spotlight 75 also suitable for rotation or removal and usable for medical diagnosis, a removable 64 battery pack 76, removable clips 77, USB hub 78 for data connectivity and power control between devices and tools within the overall intelligent medical kit, a second battery pack 79, removable fold flat 48W solar panel sheets 81 capable to be storable within the surface of the medical kit (or within wearable case 65), EKG cord and cable sub-unit 80, USB ultrasound sub-unit 82 (capable of connecting to a charger point and to the USB data and power hub 78), defibrillator sub-unit 83, and blood pressure monitors sub-unit 84, where said overall medical kit 64 or battery packs 76,79 are capable of being charged when placed in a charging and storage rack 19 by means of contact or proximity wireless charging points 63.

Although the invention has been described and illustrated with reference to example embodiments it is expressly understood that it is in no way limited to the disclosure of such example and preferred embodiments within the domain of disaster response systems, but is capable of numerous modifications within the spirit and scope of the underlying inventions. By way of reference said DMS messaging language, and local caching of data, together with DML mapping and mark-up layers, and resource ontologies may have wider application in civilian and regular commercial applications, for the provision of information services, or offering products, location, news of event activity. Similarly, UAV platforms and logistics systems herein described may have applicability in the distribution of materials and packages, or for distribution within facilities or buildings. Similar medical aid, electronic bracelets and triage systems have been described largely in the context of disaster site management but have wide applicability in large sites of ongoing crises such as famine and refugee centers, urban slums, military theatres of war, and in hospitals and assisted care monitoring of the elderly.

What is claimed is:

1. A disaster response system, comprising:
   a communication infrastructure including a plurality of sensor assemblies configured to:
      generate data indicative of at least one of environmental conditions, motion, position, chemical detection, and medical information; and
      wirelessly provide the generated data to the communication infrastructure,
      wherein at least one of the sensor assemblies generates data indicative of a position of the at least one sensor assembly;
   an incident command infrastructure configured to:
      exchange data with the communication infrastructure; and
      detect an incident based on the data from the sensor assemblies;
   an unmanned aerial vehicle (UAV) configured to deliver a payload in response to the detected incident and to a location indicated by the data from the at least one sensor assembly, wherein the at least one sensor assembly is separate from the UAV; and
   a phone device configured to:
      exchange data with the communication infrastructure;
      periodically cache a local map into a memory of the phone device responsive to the phone device entering a new zone or geographic region; and
      provide the cached local map to a user in response to the detected incident.

2. The disaster response system of claim 1, wherein at least one of the plurality of sensor assemblies is coupled to the UAV.

3. The disaster response system of claim 1, wherein the UAV is a first UAV, and wherein the system further comprises:
   a central UAV; and
   a plurality of peripheral UAVs that includes the first UAV, wherein the plurality of peripheral UAVs is configured to communicate with the central UAV.

4. The disaster response system of claim 3, wherein each of the peripheral UAVs is coupled to one of the plurality of sensor assemblies other than the at least one sensor assembly.

5. The disaster response system of claim 1, wherein the payload comprises a modular aid solution configured to aid in forest fire reduction, or wherein the payload comprises a communications unit configured to broadcast signals to support local mesh networking and communications relay support or data exchange other communications devices, or wherein the payload comprises an energy generating module, or wherein the payload comprises a modular shelter.

6. The disaster response system of claim 1, wherein the payload comprises a portable intelligent first aid diagnostic kit, wherein the portable intelligent first aid diagnostic kit comprises a thermally-insulating foil parachute, and wherein the UAV is configured to deploy the intelligent first aid diagnostic kit according to a planned trajectory, a remote-control user input, or a combination thereof.

7. The disaster response system of claim 1, wherein the UAV is further configured to actuate a function on a wearable device, an intelligent first aid diagnostic kit, or a combination thereof.

8. The disaster response system of claim 1, wherein each of the sensor assemblies comprises at least one of a cellular phone and a wearable device configured to be worn by a user.

9. The disaster response system of claim 1, wherein the incident command infrastructure is further configured to detect an incident based on one or more of historical data from one or more of the sensor assemblies, aggregated data from two or more of the sensor assemblies, and a correlation between data obtained from a first sensor assembly and data obtained from a second sensor assembly.

10. The disaster response system of claim 1, wherein the incident command infrastructure is further configured to detect at least one of:
    a step change in the first data obtained from one or more of the plurality of sensor assemblies; and
    a change in a pattern of the first data obtained from one or more of the plurality of sensor assemblies.

11. The disaster response system of claim 1, wherein one or more of the sensor assemblies comprises a wearable device configured to be worn by a user, wherein the wearable device is configured to communicate wirelessly with the communication infrastructure, and wherein the wearable device includes a sensor that is configured to detect a vital sign of the user.

12. The disaster response system of claim 11, wherein the wearable device comprises a wearable bracelet.

13. The disaster response system of claim 11, wherein the wearable device includes stored data and is configured to communicate the stored data with the communication infrastructure.

14. The disaster response system of claim 1, wherein the incident command infrastructure is configured to detect an incident based on one or more of real-time data from one or more of the sensor assemblies, humans, and computational analyses; aggregated data from two or more of the sensor assemblies, humans, and computational analyses; and a correlation between data obtained from a first sensor assembly and data obtained from a second sensor assembly.

15. A disaster response system, comprising:
    a communication infrastructure including a plurality of sensor assemblies configured to:

generate data indicative of at least one of environmental conditions, motion, position, chemical detection, and medical information; and wirelessly provide the generated data to the communication infrastructure, wherein at least one of the sensor assemblies generates data indicative of a position of the at least one sensor assembly;

an incident command infrastructure configured to:

exchange data with the communication infrastructure; and detect an incident based on the data from the sensor assemblies;

an unmanned aerial vehicle (UAV) configured to deliver a payload in response to the detected incident and to a location indicated by the data from the at least one sensor assembly, wherein the at least one sensor assembly is separate from the UAV; and a phone device configured to:

exchange data with the communication infrastructure;

periodically cache disaster-relevant information into a memory of the phone device;

periodically cache location data from a global positioning system (GPS) sensor into the memory of the phone device; and provide the disaster-relevant information and/or the location data to a user in response to the detected incident.

16. The disaster response system of claim 15, wherein the disaster-relevant information is periodically cached responsive to the phone device entering a new geographic region or a geographic region designated as a zone of risk.

17. The disaster response system of claim 15, wherein the disaster-relevant information is periodically cached in advance of a disaster occurring, and responsive to, a predicted disaster.

18. The disaster response system of claim 15, wherein the disaster-relevant information comprises one or more selected from the group consisting of: local evacuation points or routes, floor plans of local buildings, local medical resources or first aid points, proximately-located hazardous material, and advice on handling or avoiding such hazardous material.

* * * * *